(12) United States Patent
Capote et al.

(10) Patent No.: US 8,353,937 B2
(45) Date of Patent: Jan. 15, 2013

(54) SPINAL STABILIZATION SYSTEMS AND METHODS

(75) Inventors: Marco Dagoberto Capote, Memphis, TN (US); Robert S. Biscup, Ft. Lauderdale, FL (US); Charles L. Branch, Advance, NC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 696 days.

(21) Appl. No.: 11/805,051

(22) Filed: May 22, 2007

(65) Prior Publication Data
US 2008/0294194 A1 Nov. 27, 2008

(51) Int. Cl.
*A61B 17/70* (2006.01)

(52) U.S. Cl. .......................... 606/272; 606/246; 606/271

(58) Field of Classification Search .................. 606/246, 606/250–279
See application file for complete search history.

(56) References Cited

U.S. PATENT DOCUMENTS

| | | | |
|---|---|---|---|
| 2,525,217 A * | 10/1950 | Glitsch .................... 292/256.73 |
| 4,304,503 A * | 12/1981 | Gehring et al. ............... 411/389 |
| 4,690,365 A * | 9/1987 | Miller et al. ................... 248/650 |
| 4,887,595 A | 12/1989 | Heinig et al. |
| 5,002,542 A * | 3/1991 | Frigg .......................... 606/264 |
| 5,071,301 A * | 12/1991 | Engelhardt et al. ........... 411/389 |
| 5,084,049 A | 1/1992 | Asher et al. |
| 5,234,431 A | 8/1993 | Keller |
| 5,261,910 A | 11/1993 | Warden et al. |
| 5,290,288 A | 3/1994 | Vignaud et al. |
| 5,382,248 A | 1/1995 | Jacobson et al. |
| 5,429,639 A | 7/1995 | Judet |
| 5,486,176 A | 1/1996 | Hildebrand et al. |
| 5,534,002 A * | 7/1996 | Brumfield et al. ............. 606/278 |
| 5,569,247 A | 10/1996 | Morrison |
| 5,584,887 A | 12/1996 | Kambin |
| 5,607,425 A * | 3/1997 | Rogozinski ................... 606/264 |
| 5,613,967 A | 3/1997 | Engelhardt et al. |
| 5,676,703 A * | 10/1997 | Gelbard ........................ 606/305 |
| 5,707,372 A | 1/1998 | Errico et al. |
| 5,735,850 A | 4/1998 | Baumgartner et al. |
| 5,800,435 A | 9/1998 | Errico et al. |
| 5,928,233 A | 7/1999 | Apfelbaum et al. |
| 5,984,924 A | 11/1999 | Asher et al. |
| 6,273,914 B1 * | 8/2001 | Papas .......................... 623/17.11 |
| 6,302,883 B1 * | 10/2001 | Bono ............................ 606/291 |
| 6,458,132 B2 * | 10/2002 | Choi ............................. 606/267 |
| 6,524,315 B1 | 2/2003 | Selvitelli et al. |
| 6,592,311 B2 * | 7/2003 | Wojciechowski et al. ..... 411/107 |
| 6,610,062 B2 * | 8/2003 | Bailey et al. ................... 606/261 |
| 6,626,904 B1 * | 9/2003 | Jammet et al. ................. 606/266 |
| 6,641,583 B2 | 11/2003 | Shluzas et al. |
| 6,645,207 B2 | 11/2003 | Dixon et al. |
| 6,673,074 B2 | 1/2004 | Shluzas |

(Continued)

*Primary Examiner* — Eduardo C Robert
*Assistant Examiner* — Jerry Cumberledge

(57) ABSTRACT

A spinal stabilization system, apparatus, and method are disclosed which include an interconnection mechanism for engaging stabilization members to one another. In one embodiment, the interconnection mechanism comprises a locking member having first and second threaded segments. An anchor member is provided having an upper segment and a lower segment, wherein the lower segment is structurally configured for engagement with a respective bone segment. A first stabilization member is connected to the upper segment of the anchor member. A locking member is engaged with the anchor member such that the first stabilization member is fixedly secured to the anchor member by a lower portion of the locking member having a first threaded segment. A second stabilization member is connected to an upper portion of the locking member by a cap that is threaded onto a second threaded segment of the locking member.

10 Claims, 8 Drawing Sheets

U.S. PATENT DOCUMENTS

| | | |
|---|---|---|
| 6,682,530 B2 | 1/2004 | Dixon et al. |
| 6,811,364 B2 * | 11/2004 | Kelzer .......................... 411/389 |
| 6,884,241 B2 | 4/2005 | Bertranou et al. |
| 2002/0007183 A1 * | 1/2002 | Lee et al. ....................... 606/61 |
| 2002/0072750 A1 * | 6/2002 | Jackson ......................... 606/73 |
| 2002/0138077 A1 * | 9/2002 | Ferree ........................... 606/61 |
| 2003/0144665 A1 * | 7/2003 | Munting ........................ 606/61 |
| 2004/0102773 A1 * | 5/2004 | Morrison et al. ............... 606/61 |
| 2005/0080420 A1 * | 4/2005 | Farris et al. .................... 606/61 |
| 2005/0129484 A1 * | 6/2005 | Huang ........................... 411/389 |
| 2006/0025770 A1 * | 2/2006 | Schlapfer et al. .............. 606/61 |
| 2006/0064091 A1 * | 3/2006 | Ludwig et al. ................. 606/61 |
| 2006/0104742 A1 * | 5/2006 | Fleming ........................ 411/389 |
| 2006/0241595 A1 * | 10/2006 | Molz et al. ..................... 606/61 |

* cited by examiner

SPINAL STABILIZATION SYSTEMS AND METHODS

TECHNICAL FIELD

The present invention relates generally to stabilization systems and methods configured to stabilize at least a portion of the spinal column via the use of an interconnection mechanism for engaging two or more stabilization members to one another.

BACKGROUND

In the art of orthopedic surgery, and particularly spinal surgery, it has long been known to anchor one or more elongate stabilization members, such as spinal plates or rods, to a portion of the spinal column to provide stabilization and support across two or more vertebral levels. With regard to prior stabilization systems, in order to revise or add to an existing system, one or more stabilization components must be loosened and/or removed to allow for integration and attachment of additional stabilization members or devices to the system, thereby tending to increase the complexity and duration of the surgical procedure.

There remains a need for improved stabilization systems and methods. The present invention satisfies this need and provides other benefits and advantages in a novel and unobvious manner.

SUMMARY

The present invention relates generally to stabilization systems and methods configured to stabilize at least a portion of the spinal column. While the actual nature of the invention covered herein can only be determined with reference to the claims appended hereto, certain forms of the invention that are characteristic of the invention are described briefly as follows.

In one aspect of the present invention, a bone structure stabilization system is provided which is capable of stabilizing adjacent bone structures. The bone structure stabilization system includes an anchor member having an upper segment and a lower segment. The lower segment of the anchor member is structurally configured to be positioned in a respective bone segment. In one embodiment, the lower segment of the anchor member comprises an externally threaded segment that acts as a bone screw for securing the anchor member in a respective bone structure. A first stabilization member is connected to the upper segment of the anchor member. In one example, the first stabilization member comprises a rod and the upper segment of the anchor member includes a head defining a cradle portion in which a portion of the rod is positioned.

The bone structure stabilization system also includes a locking member that is engaged with the anchor member. The locking member is connected to the anchor member such that the first stabilization member is fixedly secured to the anchor member by a lower portion of the locking member. The lower portion of the locking member protrudes downwardly from a mounting segment of the locking member and includes an externally threaded segment. The anchor member includes an internally threaded segment within which the externally threaded segment of the locking member is threaded to engage the locking member with the anchor member. A lower surface of the externally threaded segment makes contact with a surface of the first stabilization member to thereby secure the first stabilization member to the anchor member.

The bone structure stabilization system also includes a second stabilization member that is connected to an upper portion of the locking member. In one example, the second stabilization member comprises a plate member having an elongated slot. The upper portion of the locking member includes an externally threaded segment about which the elongated slot is positioned. A portion of the externally threaded segment protrudes upwardly through the elongated slot and above an upper surface of the plate member. A cap is connected to the upper portion of the locking member to secure the second stabilization member to the locking member. In one embodiment, the cap includes an internally threaded segment that threads onto the externally threaded segment of the locking member that protrudes upwardly through the upper surface of the plate member to secure the plate member to the locking member.

Another aspect of the present invention is directed to a method of stabilizing adjacent bone structures. The method includes the step of inserting an anchor member into a portion of bone structure. The anchor member includes a threaded portion that is capable of threading into a portion of bone structure to fixedly secure the anchor member to the bone structure. A first stabilization member is then positioned within a cradle defined by the anchor member. The first stabilization member is secured in the cradle of the anchor member with a locking member that includes a lower mounting surface and an upper mounting surface. A threaded segment protrudes downwardly from the lower mounting surface and threads into an internally threaded segment of the anchor member. A second stabilization member is then placed on the upper mounting surface of the locking member. Once in place, the second stabilization member is secured on the upper mounting surface of the locking member with a locking cap. The cap threads onto a threaded segment protruding upwardly from the upper mounting surface.

Yet another aspect of the present invention is directed to a spinal stabilization apparatus. The spinal stabilization apparatus includes a plurality of bone anchor members positioned in respective vertebrae of a spinal column. A first stabilization member is positioned in a first set of the bone anchor members that spans from a beginning location in one vertebra to an ending location in another vertebra. A first locking member is positioned in each of the bone anchor members of the first set of bone anchor members except the bone anchor member at the ending location. The first locking member secures the first stabilization member in the first set of bone anchor members.

A dual thread locking member is positioned in the bone anchor member at the ending location. The dual thread locking member includes a mounting segment positioned between an upper externally threaded segment and a lower externally threaded segment. The lower externally threaded segment threads into an internally threaded portion of the bone anchor member at the ending location to secure the first stabilization member in the bone anchor member. A second stabilization member is positioned about the upper externally threaded segment of the dual thread locking member and a portion of the upper externally threaded segment protrudes above a surface of the second stabilization member. A locking cap is used to secure the second stabilization member to the upper externally threaded segment.

Another aspect of the present invention is directed to a method of revising an implanted spinal construct. The method includes removing a set screw from an anchor member that secures a first stabilization member to a respective bone segment. A lower portion of a locking member is then connected to the anchor member to once again secure the first stabilization member to the anchor member. A second stabilization member is then placed about an upper portion of the locking member such that a portion of a lower surface of the second stabilization member rests on an upper surface of a mounting segment of the locking member. A cap is then secured to the upper portion of the locking member to fixedly secure the second stabilization member to the upper surface of the mounting segment. This method allows constructs to be revised without requiring the removal of an existing construct, thereby reducing surgery time, recovery time, and the number of components required to perform the revision surgery.

Yet another aspect of the present invention is directed to a locking member for a bone stabilization apparatus having at least first and second stabilization members. The locking member includes a mounting segment having an upper engagement surface and a lower engagement surface. A lower threaded segment extends downwardly from the lower engagement surface of the mounting and is structurally configured to be connected with an anchor member to secure the first stabilization member within the anchor member. An upper threaded segment extends upwardly from the upper engagement surface of the mounting segment that is structurally configured to receive a second stabilization member such that a portion of the second stabilization member rests on the upper engagement surface. A locking cap having an internal threaded segment is structurally configured to thread onto the upper threaded segment to secure the second stabilization device to the upper engagement surface of the mounting segment.

It is one object of the present invention to provide stabilization systems and methods configured to stabilize at least a portion of the spinal column. Further objects, features, advantages, benefits, and aspects of the present invention will become apparent from the drawings and description contained herein.

DETAILED DESCRIPTION

Figure 1:
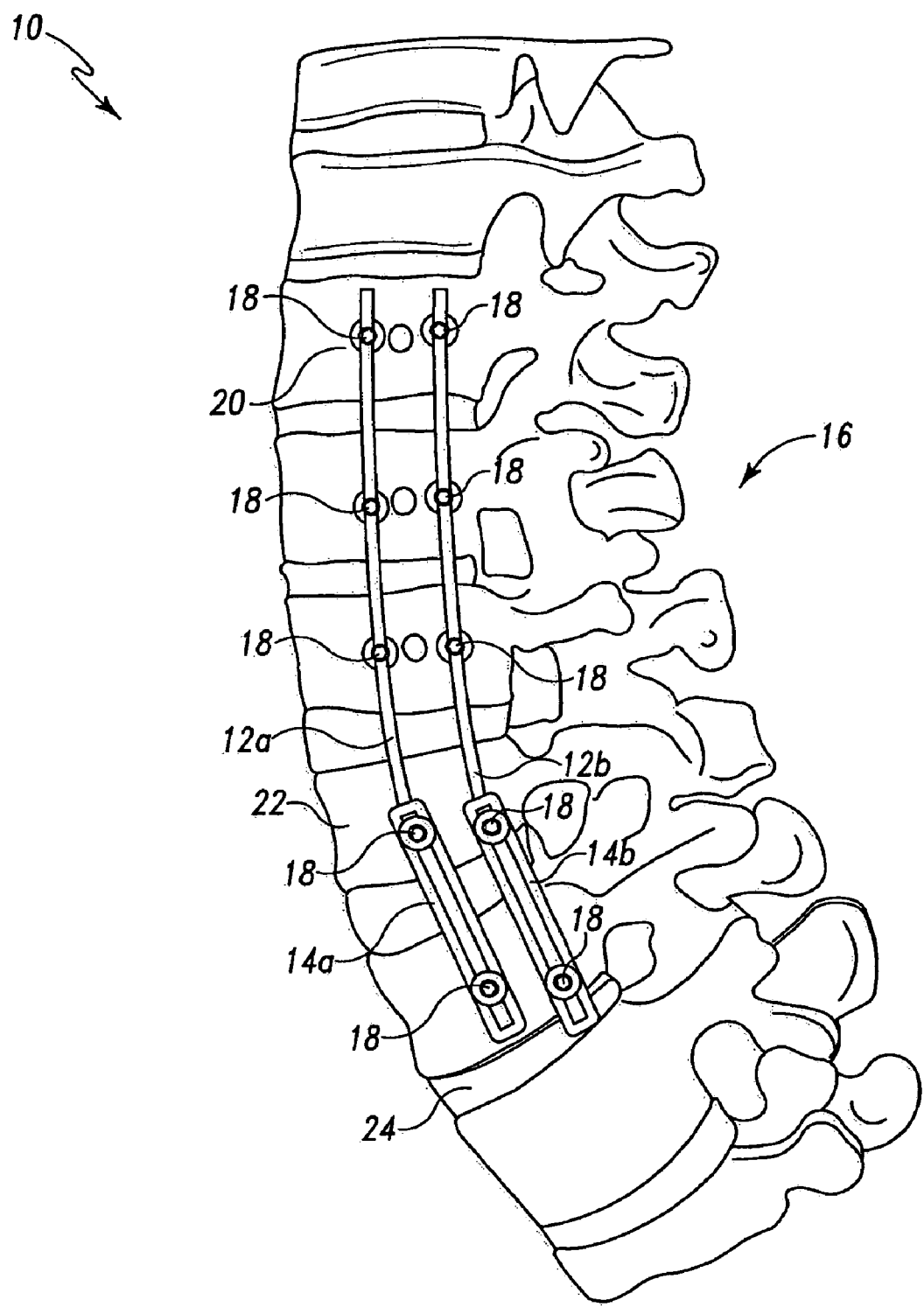
FIG. 1 illustrates a stabilization system according to one embodiment of the present invention, as engaged to a portion of the spinal column.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Referring to FIG. 1, illustrated therein is a spinal stabilization system 10 according to one form of the present invention. The stabilization system 10 generally includes first supports or stabilization members 12a, 12b engaged to a first portion of the spinal column via a number of bone anchors 18, which are in turn interconnected with second supports or stabilization members 14a, 14b engaged to a second portion of the spinal column 16 via a number of bone anchors 18. The anchor members 18 are configured to securely anchor the stabilization members 12a, 12b and 14a, 14b to respective vertebrae 22 of the spinal column 16. As will be set forth in greater detail below, in one embodiment of the invention, the anchor members 18 comprise bone screws, with locking members provided to engage the stabilization members to the bone screws. However, it should be understood that other types and configurations of anchor members are also contemplated as falling within the scope of the present invention including, for example, spinal hooks, staples, bolts or any other suitable bone anchor device that would occur to one of skill in the art.

Although the embodiment of the invention shown in FIG. 1 illustrates the stabilization system 10 engaged to a lateral aspect of the spinal column 16, it should be understood that the stabilization system 10 may be engaged to other portions of the spinal column 16, including posterior or anterior portions. Additionally, it is also contemplated that the present invention may have application in other parts of the human body including, for example, other types of joints or long bones. The particular arrangement of the stabilization members 12a, 12b and 14a, 14b is determined by the surgeon before and/or during the surgical procedure to conform the stabilization system 10 to the patient's anatomy and to provide relief for the patient's diagnosed medical condition. It should be understood, however, that the particular arrangement of the first and second stabilization members 12a, 12b and 14a, 14b is exemplary, and may be adjusted or changed to provide any desired stabilization arrangement or configuration.

In the illustrated embodiment of the invention, the first stabilization members 12a, 12b comprise elongate spinal rods. Although a conventional circular-shaped spinal rod is illustrated, it should be appreciated that other shapes and configurations are also contemplated, including square, rectangular, hexagonal, diamond and elliptical shaped rods, or any other suitable shape that would occur to one of skill in the art. The spinal rod 12a, 12b may be formed from stainless steel, titanium, polyetherketone (PEEK), or any other suitable biocompatible material known to those of skill in the art. In the illustrated embodiment, the stabilization system 10 includes a pair of spinal rods 12a, 12b running substantially parallel to one another along the spinal column 16. However, in other embodiments, a single spinal rod may be used. Additionally, it should be understood that the stabilization members 12a, 12b may take on other configurations including, for example, plates, wires, tethers, or any other suitable configuration known to those of skill in the art.

Figure 2:
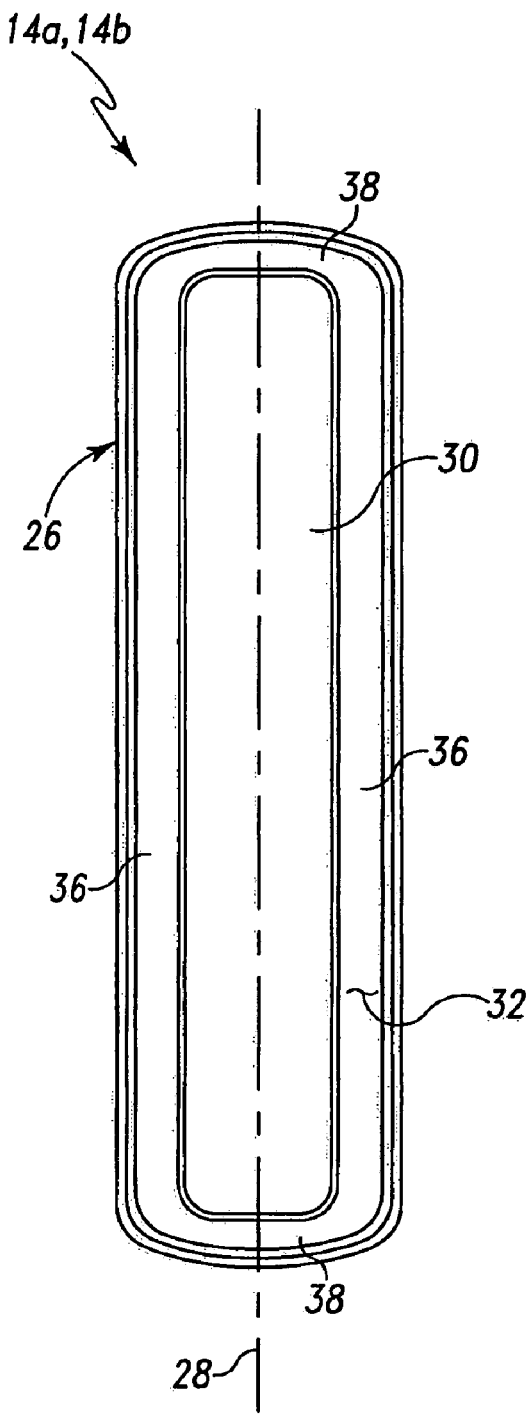
FIG. 2 is a top view of a stabilization member according to one embodiment of the present invention.
Figure 3:
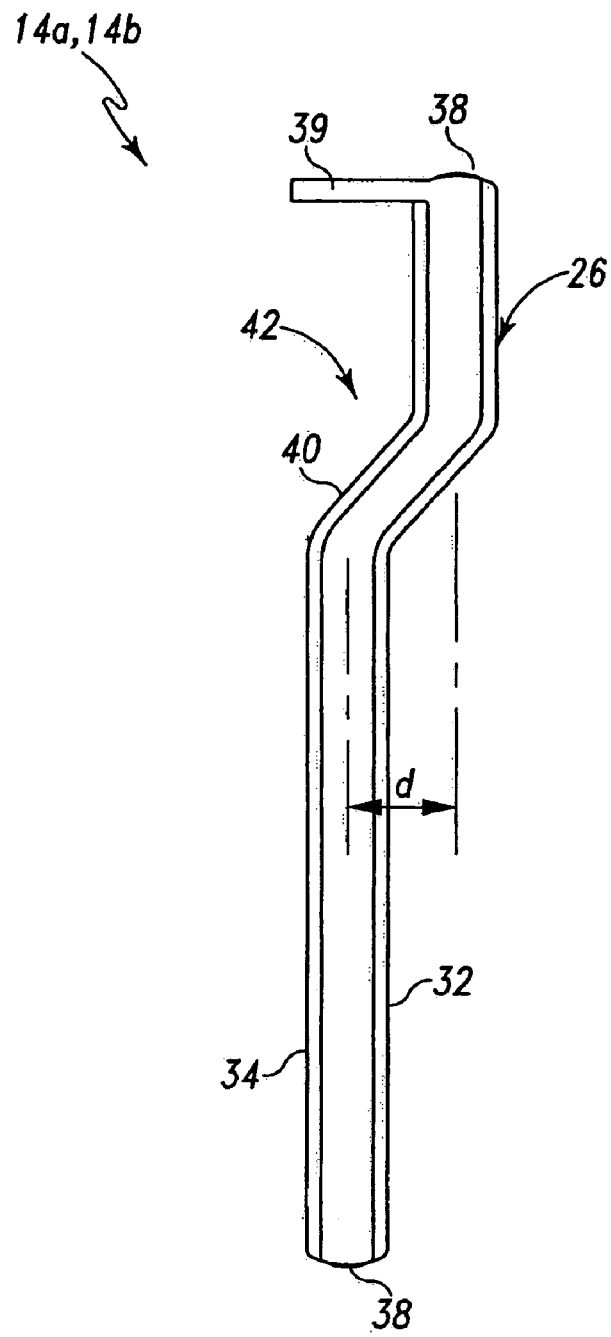
FIG. 3 is a side view of the stabilization member illustrated in FIG. 2.
Figure 7:
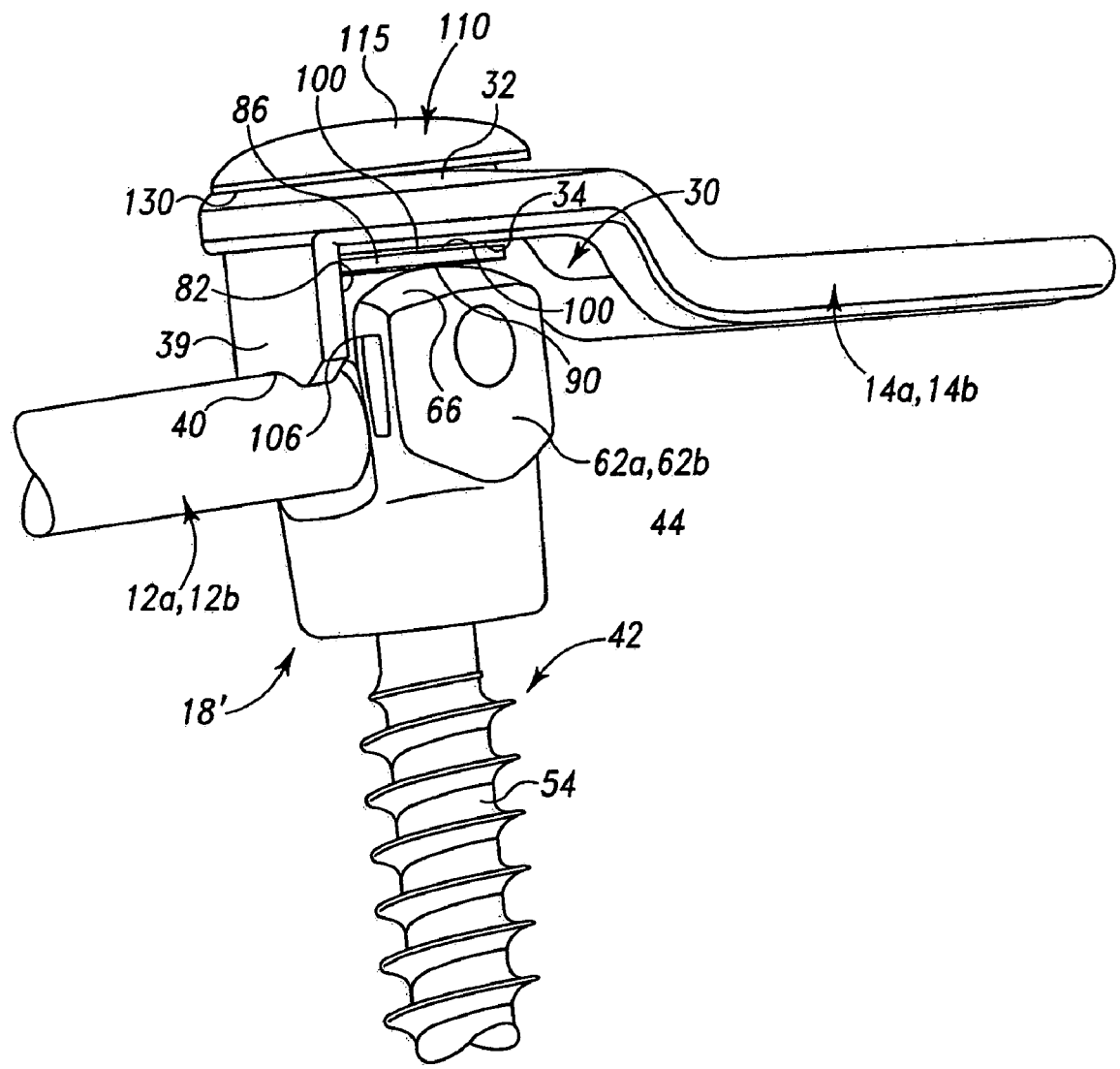
FIG. 7 illustrates a stabilization assembly according to another embodiment of the present invention including first and second stabilization members engaged with an anchor member by a locking member.

Referring collectively to FIGS. 2 and 3, in one embodiment of the invention, the second stabilization members 14a, 14b comprise plate members. The plate members 14a, 14b include an elongate body 26 extending along a longitudinal axis 28. In the illustrated embodiment, the elongate body 26 includes at least one opening in the form of an elongate slot 30 extending generally along the longitudinal axis 28. The elongate slot 30 extends through the elongate body 26 between upper and lower surfaces 32, 34, thereby defining side rails 36 extending longitudinally along opposite sides of the elongate slot 30, and a pair of end rails 38 extending transversely between the side rails 36 adjacent the ends of the elongate body 26. The plate members 14a, 14b further include a flange portion 39 extending downwardly from one of the end rails 38. As illustrated in FIG. 7, the flange portion 39 includes a lower engagement surface 40 configured to conform to an outer surface of the spinal rods 12a, 12b. In the illustrated embodiment, the engagement surface 40 has a curved or concave configuration which conforms with an outer curved surface of the spinal rods 12a, 12b. However, other shapes and configurations are also contemplated. In the illustrated embodiment, the plate member 14a, 14b include a curved or angled section 42 which interconnect first and second portions of the body 26 that are offset from one another by a distance d. In other embodiments, the plate member 14a, 14b need not include a curved or angled section, but may instead be provided with a generally flat or planar configuration.

Although a particular configuration of the stabilization members 14a, 14b has been illustrated and described herein, it should be appreciated that other plate configurations are also contemplated as falling within the scope of the present invention. Additionally, it should be understood that the stabilization members 14a, 14b may take on other configurations including, for example, rods, wires, tethers, or any other suitable configuration known to those of skill in the art. The stabilization members 14a, 14b may be formed from stainless steel, titanium, polyethertherketone (PEEK), or any other suitable biocompatible material known to those of skill in the art. In the illustrated embodiment, the stabilization system 10 includes a pair of plate members 14a, 14b running substantially parallel to one another along the spinal column 16. However, in other embodiments, a single plate member may be used.

Figure 4:
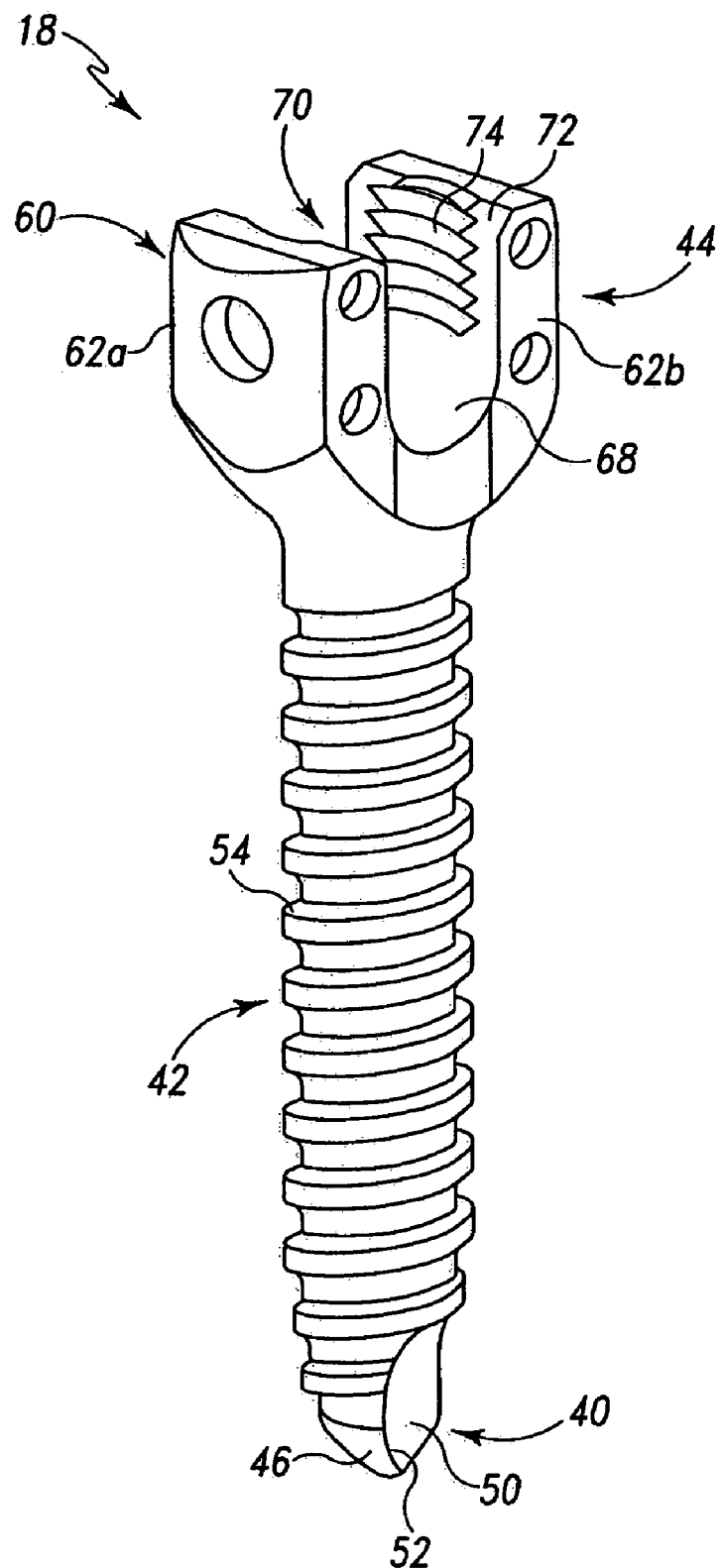
FIG. 4 is a side perspective view of an anchor member according to one embodiment of the present invention.

The spinal rods 12a, 12b and the plate members 14a, 14b are engaged to the spinal column 16 via a plurality of anchor members 18, which as indicated above may be configured as bone screws. Referring to FIG. 4, shown therein is one embodiment of an anchor member 18 suitable for use in association with the present invention. The anchor member 18 extends generally along a longitudinal axis and includes a distal segment 40, an intermediate threaded segment 42, and a proximal fixation or connection segment 44. The distal segment 40 may be provided with self-cutting or self-drilling capabilities, including a tip 46 defining a cutout or flute 50 providing a cutting edge 52. The threaded segment 42 defines a helical thread 54 configured for anchoring in bone, and more particularly in cancellous bone. In the illustrated embodiment, the fixation segment 44 comprises a head 60 having a pair of generally parallel arms 62a, 62b that provide a cradle 68 defining a generally U-shaped channel 70 between the arms 62a, 62b for receiving the first stabilization member or spinal rod 12a, 12b. An interior surface 72 of the arms 62a, 62b defines inner threads 74 for receiving a set screw such as, for example, a conventional set screw 19 (FIG. 1) for capturing the spinal rod 12a, 12b within the cradle 68 and U-shaped channel 70 of the bone anchor 18. Although a particular configuration of a bone anchor 18 has been illustrated and described herein, it should be understood that other types and configurations are also contemplated.

Figure 5:
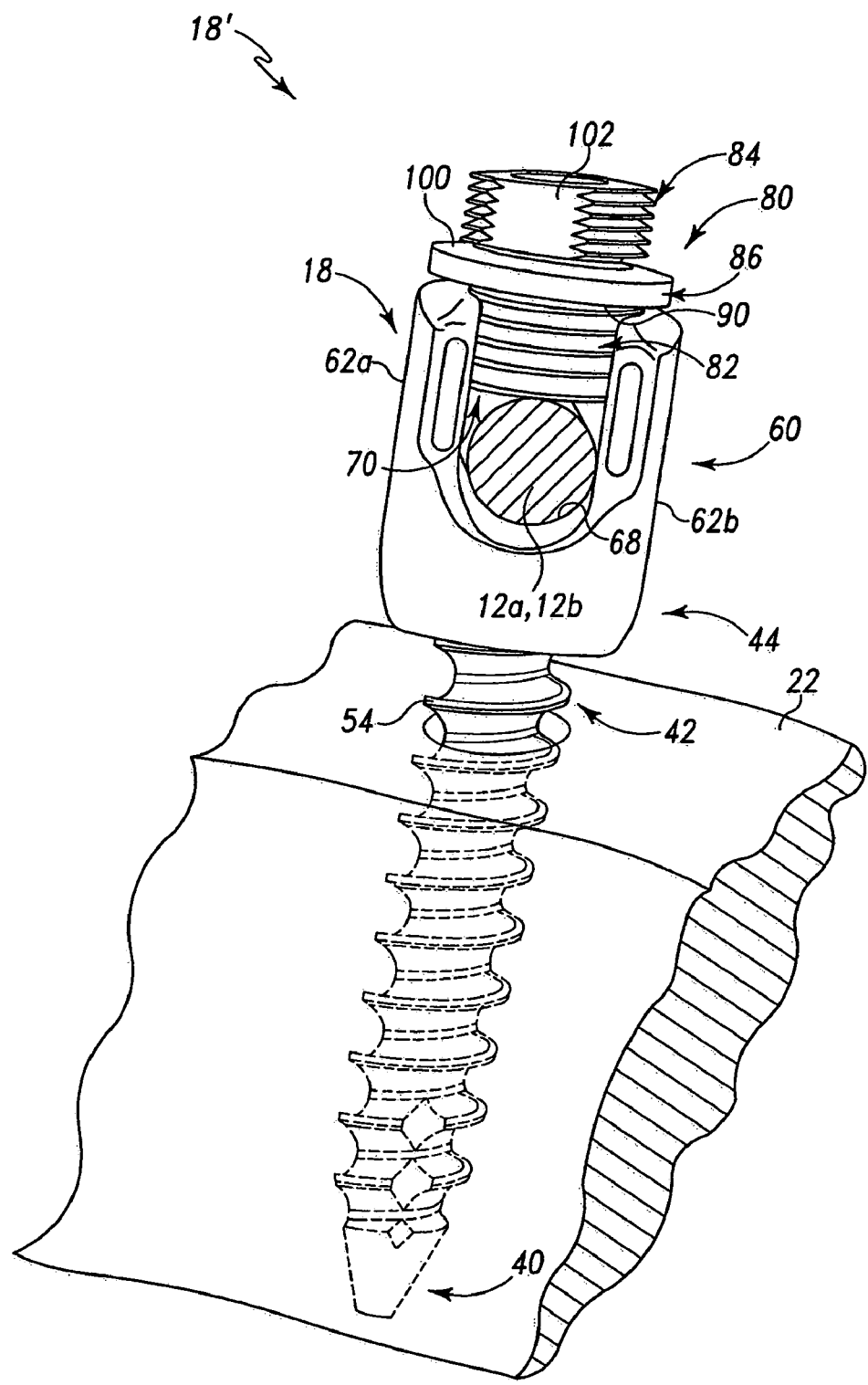
FIG. 5 illustrates a stabilization assembly according to another embodiment of the present invention including an elongate stabilization member engaged with an anchor member by a locking member.

Referring to FIG. 5, shown therein is another embodiment of an anchor member 18' suitable for use in association with the present invention. The anchor member 18' is also configured as a bone screw and, like the bone screw 18, includes a distal segment 40, an intermediate threaded segment 42 defining a helical thread 54, and a proximal fixation or connection segment 44 including a head 60 having a pair of generally parallel arms 62a, 62b that provide a cradle 68 defining a generally U-shaped channel 70 for receiving one of the spinal rod 12a, 12b. Additionally, like the bone screw 18, the interior surfaces of the arms 62a, 62b define inner threads for receiving a locking member or set screw for capturing the spinal rod 12a, 12b within the cradle 68 and U-shaped channel 70 of the bone anchor 18'. However, unlike the bone screw 18 which has a single-piece configuration, the bone screw 18' has a poly-axial configuration wherein the connection segment 44 is formed separately from the threaded segment 42 and is attached thereto in a manner which allows the connection segment 44 to pivot or rotate relative to the threaded segment 42 prior to being locked at a selected angular and/or rotational position. Poly-axial bone screws are well know to those of skill in the art and need not be discussed in further detail herein. Although a particular configuration of the poly-axial bone anchor 18' has been illustrated and described herein, it should be understood that other types and configurations are also contemplated.

Figure 6:
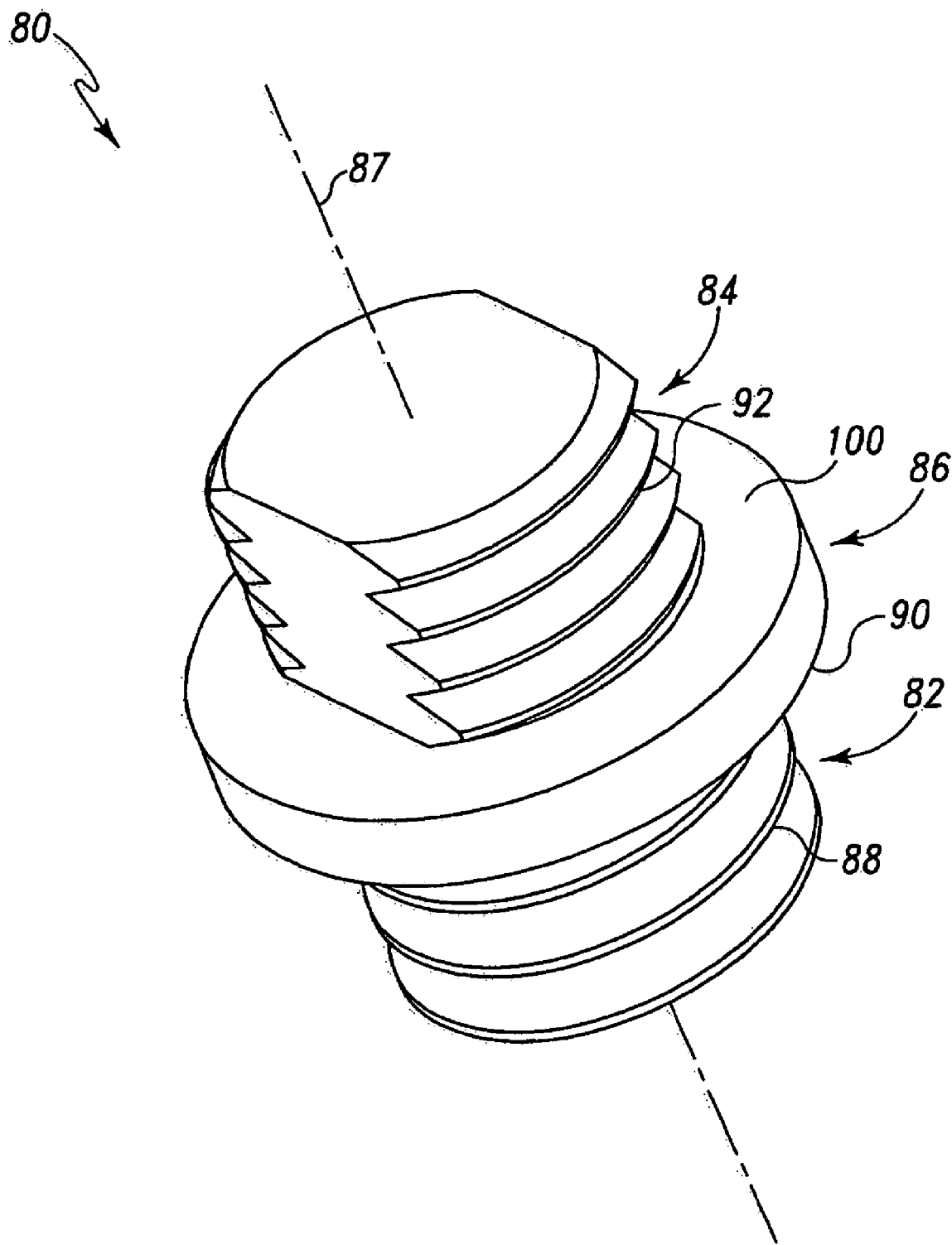
FIG. 6 is a perspective view of the locking member illustrated in FIG. 5.

Referring collectively to FIGS. 5 and 6, shown therein is a locking member 80 according to one embodiment of the present invention for securing one of the spinal rods 12a, 12b within the cradle 68 and U-shaped channel 70 of the bone anchor 18, 18', and for coupling one of the plate members 14a, 14b to the bone anchor 18, 18'. In the illustrated embodiment, the locking member 80 comprises a dual-threaded member including a lower threaded segment 82 and an upper threaded segment 84 that are separated from one another by an intermediate contact or mounting segment 86. The locking member 80 extends generally along an axis 87, with the upper and lower threaded segments 82, 84 extending axially from the mounting segment 86 in generally opposite directions.

Figure 8:
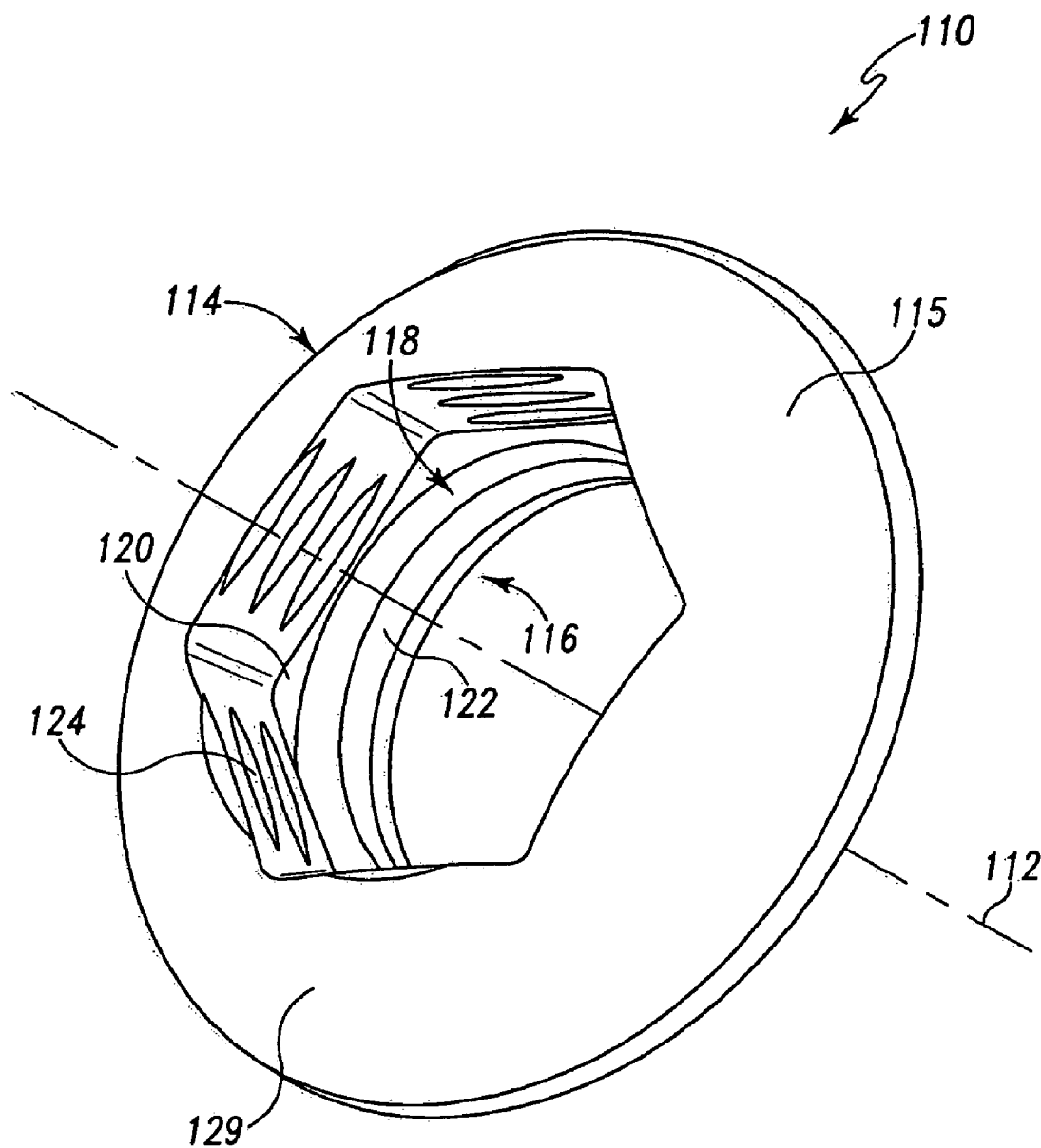
FIG. 8 is a side perspective view of a locking cap portion of the locking member illustrated in FIG. 7.
Figure 9:
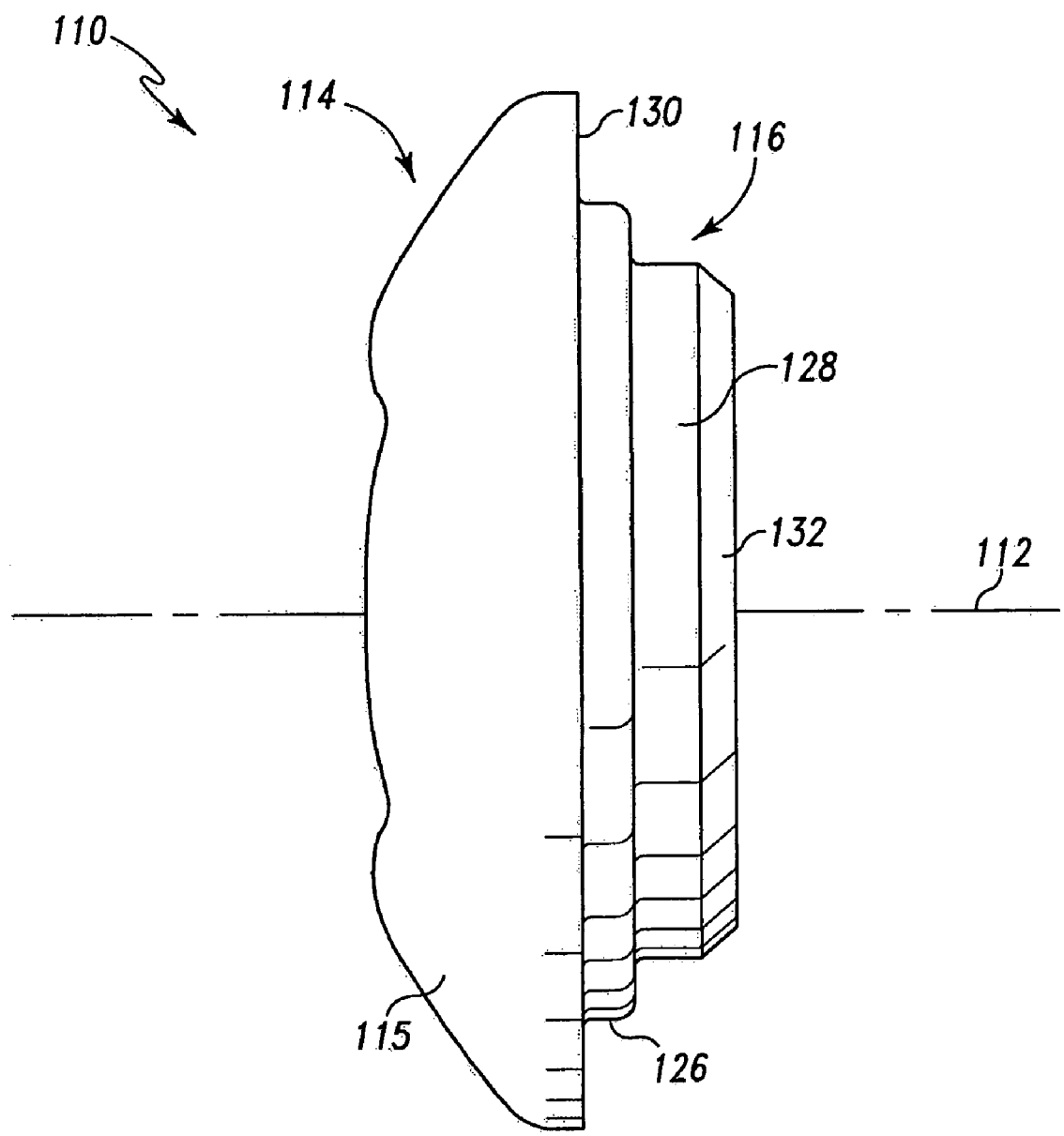
FIG. 9 is a side view of the locking cap portion illustrated in FIG. 8.

The lower threaded segment 82 includes external threads 88 that are configured for threading engagement with the internal threads 74 formed along the arms 62a, 62b of the bone anchor 18, 18'. The length of the lower threaded segment 82 may be sized such that a lower surface 90 of the intermediate mounting segment 86 engages an upper surfaces 66 of the arms 62a, 62b of the bone anchor 18, 18', while at the same time exerting sufficient force against the spinal rod 12a, 12b to secure the spinal rod 12a, 12b in position relative to the bone anchor 18, 18'. The upper threaded segment 84 includes external threads 92 that are configured for threading engagement within a threaded passage formed in a locking cap or nut 110 (FIGS. 8 and 9). The upper threaded segment 84 further includes a pair of opposing flat or truncated surfaces 102 that are engagable by a tool or wrench. The length of the upper threaded segment 82 is sized to extend into the elongate slot 30 defined by the plate member 14a, 14b, with an upper surface 100 of the intermediate mounting segment 86 engaging a lower surface 34 of the plate member 14a, 14b. Although the external threads 88, 92 formed along the upper and lower threaded segments are illustrated as having a particular thread configuration, it should be understood that various thread configurations are contemplated including, for example, a buttress thread, a helical thread, a square thread, a reverse-angle thread or other thread-like structures.

Referring collectively to FIGS. 7-9, shown therein is a locking cap or nut 110 according to one embodiment of the present invention. The locking cap 100 is generally circular in shape and extends generally along an axis 112. In the illustrated embodiment, the locking cap 100 includes an upper portion 114, a lower portion 116, and an axial passage 118 extending through the upper and lower portions 114, 116. A first portion of the axial passage 118 extending through the upper portion 114 of the locking cap 110 has a hexagonal shape configured for engagement with a driving tool and terminates at a base or shoulder 120. A second portion of the axial passage 118 extending through the lower portion 116 of the locking cap 110 has a circular shape and defines internal threads 122 configured for threading engagement with the external threads 92 formed along the upper threaded segment 84 of the locking member 80. The first portion of the axial passage 118 extending through the upper portion 114 of the locking cap 110 may be provided with a series of notches or grooves 124 that provide frictional engagement with the driving tool and/or which aid in engaging or securing a lid or cover (not shown) to the locking cap 110 to close off the axial passage 118.

As illustrated in FIG. 9, the upper portion 114 of the locking cap 110 defines a curved or rounded upper surface 115 devoid of sharp edges or corners to avoid injury or trauma to adjacent tissue. The lower portion 116 of the locking cap 110 includes a first cylindrical portion 126 having a diameter sized somewhat smaller than the upper portion 114 of the locking cap 110, thereby defining a lower surface or shoulder 130. The diameter of the first cylindrical portion 126 is preferably sized in relatively close tolerance with the width of the elongate slot 30 extending through the plate members 14a, 14b. The lower portion 116 of the locking cap 110 further includes a second cylindrical portion 128 extending from the first cylindrical portion 126 and having a diameter sized somewhat smaller than the first cylindrical portion 126. The end of the second cylindrical portion 128 may be provided with a tapered edge 132. As shown in FIG. 7, when the locking cap 110 is threaded onto the upper threaded segment 84 of the locking member 80, the lower surface or shoulder 130 of the cap 110 engages the upper surface 32 of the plate member 14a, 14b, thereby forcing the plate member 14a, 14b into tight engagement against the upper surface 100 of the locking member 80, and also firmly engaging the lower engagement surface 40 of the flange 39 against the outer surface of the spinal rod 12a, 12b. Although a particular configuration of the locking cap 110 has been illustrated and described herein, it should be understood that other configurations are also contemplated as falling within the scope of the present invention.

In one embodiment of the invention, stabilization members 12a, 12b may comprise a stabilization system that has previously anchored to a first portion of the spinal column 16 by a number of bone anchors 18, 18' via a prior surgical procedure. In some instances, correction or stabilization of another portion of the spinal column is required or desired. In such instances, additional stabilization members 14a, 14b may be engaged with the stabilization members 12a, 12b and anchored to another portion of the spinal column 16 by additional bone anchors 18, 18' to provide further stabilization or support to the spinal column. Such procedures are sometimes referred to as a revision procedure or technique. During a revision procedure, benefits or advantages may be realized by avoiding removal or extensive manipulation of the previously implanted stabilization system.

Referring collectively to FIGS. 1, 5 and 7, in one embodiment of the invention, the conventional set screws 19 may be removed from the bone anchors 18, 18' adjacent one end of the existing stabilization system. The removed set screws 19 are then replaced with locking members 80, with the lower threaded segment 82 of each locking member 80 threadedly engaged along the internal threads 74 formed along the arms 62a, 62b of a respective bone anchor 18, 18' and into engagement with the spinal rod 12a, 12b to once again securely engage the spinal rods 12a, 12b to the existing bone anchors 18, 18'. The plate members 14a, 14b are then engaged to the bone anchors 18, 18' via insertion of the upper threaded segment 84 of the locking member 80 into the elongate slot 30, with the lower surface 34 of the plate member 14a, 14b resting upon the upper surface 100 of the intermediate mounting segment 86 of the locking member 80. A locking cap 110 is then threaded onto the upper threaded segment 84 of each locking member 80 until the lower surface or shoulder 130 of the cap 110 tightly engages the upper surface 32 of the plate member 14a, 14b, thereby forcing the plate member 14a, 14b into tight engagement against the upper surface 100 of the locking member 80, and also firmly engaging the lower engagement surface 40 of the flange 39 against the outer surface of the spinal rod 12a, 12b. Additional bone anchors 18, 18' are used to anchor the opposite ends of the plate members 14a, 14b to another portion of the spinal column. As should be appreciated, the plate members 14a, 14b are interconnected with the existing spinal stabilization system (including the spinal rods 12a, 12b and the existing bone anchors 18, 18') without extensive manipulation or removal of the components associated with the existing stabilization system.

While the invention has been illustrated and described in detail in the drawings and foregoing description, the same is to be considered as illustrative and not restrictive in character.

What is claimed is:

1. A bone stabilization apparatus, comprising:
    a plurality of bone anchor members configured for anchoring to a plurality of bone segments and including a first bone anchor member and a last bone anchor member;
    a first stabilization member extending between a first end portion and a second end portion, said first stabilization member being arranged in a first set of said bone anchor members spanning from said first bone anchor member to an intermediate bone anchor member positioned between said first bone anchor member and said last bone anchor member such that said first end portion is positioned in said first bone anchor member and said second end portion is positioned in said intermediate bone anchor;
    a plurality of first locking members wherein one of said plurality of first locking members is positioned in each of said bone anchor members in said first set except said intermediate bone anchor member, wherein said first locking member secures said first stabilization member in each of said first set of bone anchor members except said intermediate bone anchor member;
    a dual thread locking member positioned in said intermediate bone anchor member, wherein said dual thread locking member includes a mounting segment positioned between an upper externally threaded segment and a lower externally threaded segment, wherein said lower externally threaded segment threads into an internally threaded portion of said intermediate bone anchor member to secure said first stabilization member to said intermediate bone anchor member;
    a second stabilization member positioned about said upper externally threaded segment of said dual thread locking member and extending between said intermediate bone anchor member and one of said plurality of bone anchor members adjacent to said intermediate bone anchor member; and
    a cap for securing said second stabilization member to said upper externally threaded segment.

2. The apparatus of claim 1, wherein said bone anchor members include an upper segment and a lower segment.

3. The apparatus of claim 2, wherein said lower segment includes a threaded portion for securing said anchor member in said adjacent bone segments.

4. The apparatus of claim 2, wherein said upper segment includes a head defining a cradle portion for receiving said first stabilization member.

5. The apparatus of claim 4, wherein said head comprises a pair of upwardly opposing arms that define said cradle portion.

6. The apparatus of claim 5, wherein said upwardly opposing arms include an internally threaded segment, wherein said lower externally threaded segment of said dual thread locking member screws into said internally threaded segment of said upwardly opposing arms to secure said first stabilization member in said bone anchor members.

7. The apparatus of claim 1, wherein a portion of said upper externally threaded segment of said dual thread locking member protrudes upwardly from an upper surface of said second stabilization member.

8. The apparatus of claim 7, wherein said cap includes an internally threaded segment, wherein said internally threaded segment of said cap threads onto said upper externally threaded segment of said dual thread locking member to secure said second stabilization member to said dual thread locking member.

9. The apparatus of claim 1, wherein a portion of said upper externally threaded segment includes a pair of opposing flat surfaces.

10. The apparatus of claim 1, wherein an upper portion of said cap includes a tool receiving segment.

* * * * *